(12) United States Patent
Lecuivre et al.

(10) Patent No.: US 8,418,508 B2
(45) Date of Patent: Apr. 16, 2013

(54) ISOELASTIC POROUS MESH

(75) Inventors: Julie Lecuivre, Le Bois d'Oingt (FR); Karine Trogneux, Villeurbanne (FR)

(73) Assignee: Sofradim Production, Trevoux (FR)

( * ) Notice: Subject to any disclaimer, the term of this patent is extended or adjusted under 35 U.S.C. 154(b) by 0 days.

(21) Appl. No.: 13/500,322

(22) PCT Filed: Oct. 4, 2010

(86) PCT No.: PCT/IB2010/002802
§ 371 (c)(1),
(2), (4) Date: Apr. 5, 2012

(87) PCT Pub. No.: WO2011/042811
PCT Pub. Date: Apr. 14, 2011

(65) Prior Publication Data
US 2012/0198894 A1    Aug. 9, 2012

Related U.S. Application Data

(60) Provisional application No. 61/248,570, filed on Oct. 5, 2009.

(51) Int. Cl.
*D04B 21/20* (2006.01)

(52) U.S. Cl.
USPC .................................... 66/195; 66/170

(58) Field of Classification Search .............. 66/195, 66/170, 192, 203, 204, 205, 207, 233, 169 R; 623/1.5, 23.71; 606/151
See application file for complete search history.

(56) References Cited

U.S. PATENT DOCUMENTS

| | | | | | |
|---|---|---|---|---|---|
| 3,124,136 | A | * | 3/1964 | Usher | 606/213 |
| 5,456,711 | A | * | 10/1995 | Hudson | 623/1.5 |
| 5,569,273 | A | * | 10/1996 | Titone et al. | 606/151 |
| 5,771,716 | A | * | 6/1998 | Schlussel | 66/195 |
| 6,287,316 | B1 | * | 9/2001 | Agarwal et al. | 606/151 |
| 6,408,656 | B1 | | 6/2002 | Ory et al. | |
| 6,443,964 | B1 | * | 9/2002 | Ory et al. | 606/151 |
| 6,971,252 | B2 | * | 12/2005 | Therin et al. | 66/170 |
| 7,021,086 | B2 | * | 4/2006 | Ory et al. | 66/195 |
| 7,402,174 | B2 | * | 7/2008 | Dong | 623/1.5 |
| 7,614,258 | B2 | * | 11/2009 | Cherok et al. | 66/192 |
| 7,900,484 | B2 | * | 3/2011 | Cherok et al. | 66/192 |
| 8,157,821 | B2 | * | 4/2012 | Browning | 606/151 |
| 8,157,822 | B2 | * | 4/2012 | Browning | 606/151 |
| 2004/0029478 | A1 | * | 2/2004 | Planck et al. | 442/318 |
| 2004/0176658 | A1 | * | 9/2004 | McMurray | 600/37 |
| 2005/0228408 | A1 | * | 10/2005 | Fricke et al. | 606/151 |

FOREIGN PATENT DOCUMENTS

FR    2 880 634 A1    7/2006

OTHER PUBLICATIONS

International Search Report for Application No. PCT/IB2010/002802 mailed Apr. 20, 2011.

* cited by examiner

*Primary Examiner* — Danny Worrell

(57) ABSTRACT

Isoelastic porous meshes useful in hernia repair have pores that remain open under physiological loads.

10 Claims, 5 Drawing Sheets

US 8,418,508 B2

ISOELASTIC POROUS MESH

CROSS-REFERENCE TO RELATED APPLICATIONS

This application is a U.S. National Stage Application filed under 35 U.S.C. §371(a) of International Application No. PCT/IB2010/002802 filed Oct. 4, 2010, which claims the benefit of and priority to U.S. Provisional Application Ser. No. 61/248,570 filed Oct. 5, 2009, the entire contents of which are incorporated by reference herein.

BACKGROUND

The present disclosure relates to an isoelastic porous mesh capable of maintaining mesh porosity under small physiological loads.

Biocompatible meshes are used in many surgical procedures, for example, in the treatment of parietal insufficiencies such as hernias. The meshes are designed to provide reinforcement and support to defective tissue during the healing process. While some meshes are rigid, meshes designed to flex with the surrounding tissue tend to cause less postoperative pain. Flexible meshes are typically made of polymeric materials formed into a porous mesh. To achieve ingrowth by the surrounding tissue, the pores of the mesh must remain open. However, as a mesh flexes, the porosity of the mesh may be reduced thereby reducing ingrowth of tissue.

SUMMARY

The present disclosure relates to an isoelastic porous mesh including a biocompatible polymer filament, wherein 90% of the porosity of the mesh is provided by pores having a diameter of greater than 1 mm. In embodiments, pores having a diameter of greater than 1 mm are retained even under physiological loads. The isoelastic porous mesh may be knitted on a knitting machine according to a front bar knitting scheme of 1-0/1-2/1-0/2-3/2-1/2-3/4-5/4-3/4-5/3-2/3-4/3-2// and a rear bar knitting scheme of 4-5/4-3/4-5/3-2/3-4/3-2/1-0/1-2/1-0/2-3/2-1/2-3//.

The disclosure further includes a method of forming an isoelastic porous mesh. The method includes knitting a mesh according to a front bar knitting scheme of 1-0/1-2/1-0/2-3/2-1/2-3/4-5/4-3/4-5/3-2/3-4/3-2// and a rear bar knitting scheme of 4-5/4-3/4-5/3-2/3-4/3-2/1-0/1-2/1-0/2-3/2-1/2-3//.

The present disclosure also relates to an isoelastic porous mesh. The isoelastic porous mesh has a polyethylene terephthalate monofilament knitted to form a mesh. The mesh includes principal pores having a diameter greater than about 1.5 mm, wherein the diameter of said principal pores remains greater than 1 mm under a load of about 25 N.

BRIEF DESCRIPTION OF THE DRAWINGS

Embodiments of the disclosure will become more apparent from the reading of the following description in connection with the accompanying drawings, in which.

DETAILED DESCRIPTION

Isoelastic porous meshes in accordance with the present disclosure are capable of maintaining porosity under physiological loads, in embodiments, maintaining pore sizes of at least 1 mm under physiological loads. The present knitted isoelastic porous meshes have isotropic elastic mechanical properties. As used herein the phrase "isotropic elastic mechanical properties" means that the tensile elongation of the mesh is substantially equivalent in all directions. As used herein the phrase "substantially equivalent" means that the value of a measured property is within 10% of the value of another measurement of that property. Additionally, the present isoelastic porous meshes are capable of maintaining a high porosity allowing for better tissue ingrowth following surgery.

In embodiments, the present isoelastic porous meshes are an open knit mesh formed using a biocompatible filament or yarn. The pattern of the knit is defined by front lap and rear lap of monofilaments knit together to form the mesh. The pattern forms a plurality of pores each having a substantially circular shape. In the present application, the diameter of a pore is defined as being the diameter of the substantially circular shape of the pore.

In embodiments, the isoelastic porous mesh comprises a biocompatible polymer filament knit on a knitting machine according to a front bar knitting scheme of 1-0/1-2/1-0/2-3/2-1/2-3/4-5/4-3/4-5/3-2/3-4/3-2// and a rear bar knitting scheme of 4-5/4-3/4-5/3-2/3-4/3-2/1-0/1-2/1-0/2-3/2-1/2-3//.

The biocompatible polymer may be selected from the group consisting of biodegradable polymers, non-biodegradable polymers, and combinations thereof. In embodiments, the biocompatible polymer is a non-biodegradable polymer. For example, the biocompatible polymer is a polyester. In embodiments, the polyester is polyethylene terephthalate.

In embodiments, the biocompatible polymer filament is a monofilament, for example having a diameter of from about 0.05 mm to about 0.15 mm.

In embodiments, the mesh has a porosity and at least 90% of the porosity comprises pores having a diameter of from about 1.0 mm to about 2 mm under no load. In embodiments, the diameter of the pores having a diameter of from about 1.0 mm to about 2 mm remains greater than about 1.0 mm under a load of about 25 N.

The invention also relates to an isoelastic porous mesh comprising a polyethylene terephthalate monofilament knitted to form a mesh comprising principal pores having a diameter greater than about 1.5 mm, wherein the diameter of said principal pores remains greater than 1 mm under a load of about 25 N. In embodiments, the principal pores comprise greater than about 90% of mesh porosity.

The invention further relates to a method of forming an isoelastic mesh comprising knitting a mesh according to a front bar knitting scheme of 1-0/1-2/1-0/2-3/2-1/2-3/4-5/4-3/4-5/3-2/3-4/3-2// and a rear bar knitting scheme of 4-5/4-3/4-5/3-2/3-4/3-2/1-0/1-2/1-0/2-3/2-1/2-3//.

Figure 1:
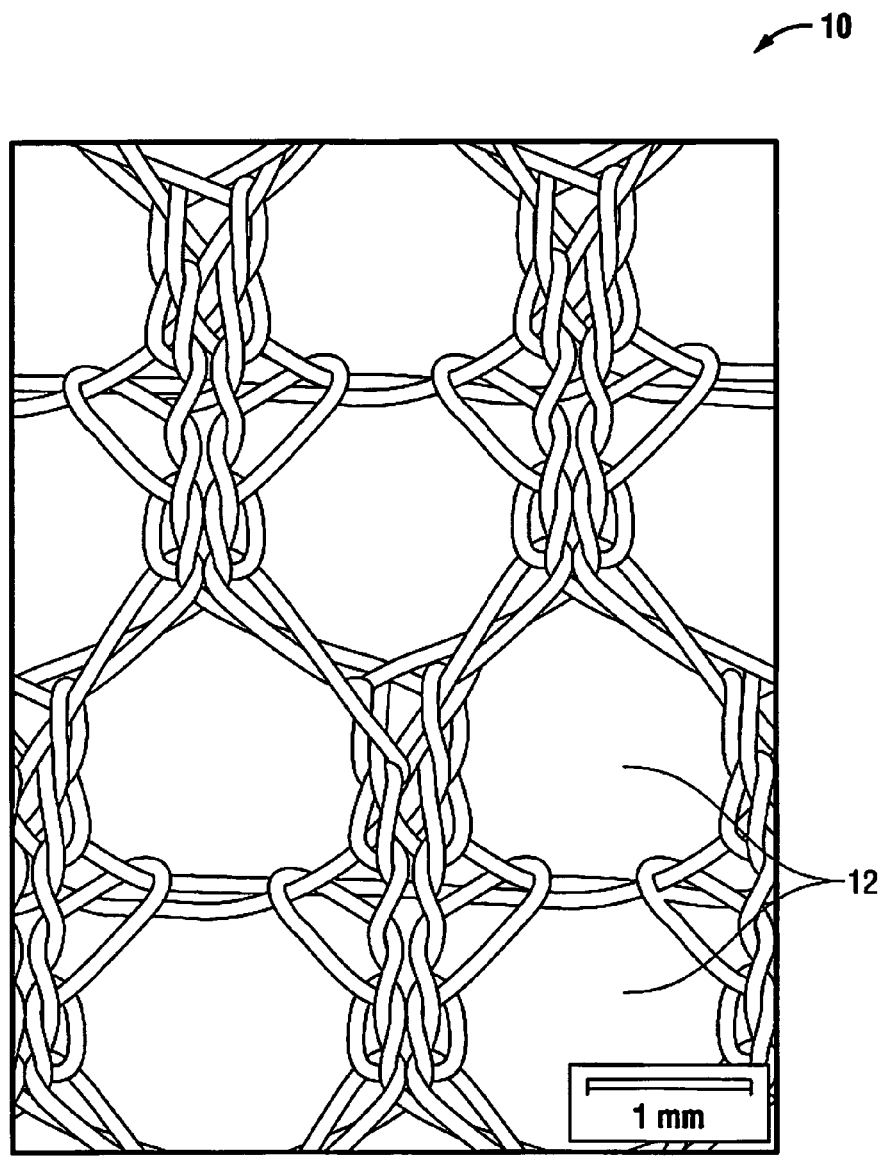
FIG. 1 is a front view of an isoelastic porous mesh in accordance with the present disclosure.

Referring now in specific detail to the drawings, in which like numbers identify similar or identical elements, FIG. 1 is a front view of one embodiment of an isoelastic porous mesh 10 in accordance with the present disclosure. The principal pores 12 are the source of more than 90% of the porosity of the mesh. The size and quantity of these principal pores 12, increase the elasticity of the mesh and allow greater tissue ingrowth in situ. In embodiments, the principal pores 12 have a diameter from about 1.0 mm to about 2.0 mm, in embodiments from about 1.3 mm to 1.5 mm. The warp knitted mesh is made of columns of stitches linked together by floats. One column of stitches is knitted using one needle. All the stitches of a same course are knitted at the same time. Once the first course is knitted, the second course is knitted, and so on.

Figure 2A:
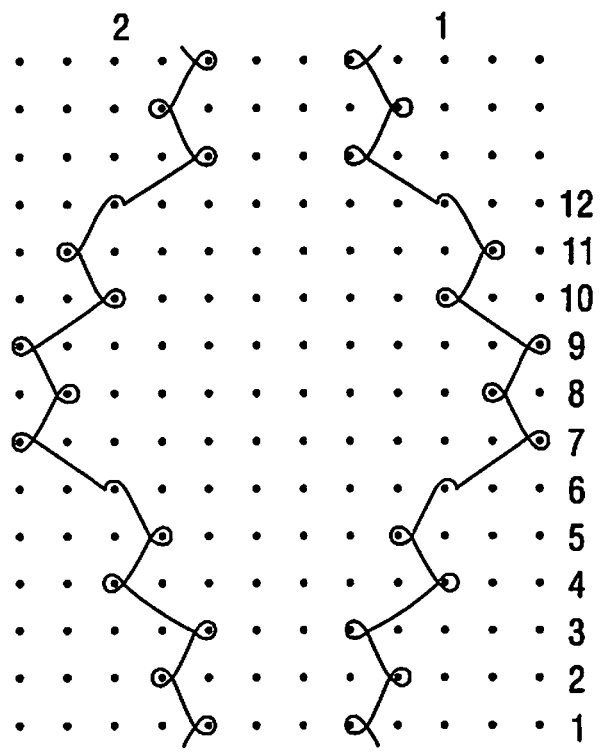
FIG. 2 is a schematic of the overall pattern of an isoelastic porous mesh in accordance with the present disclosure.
Figure 2B:
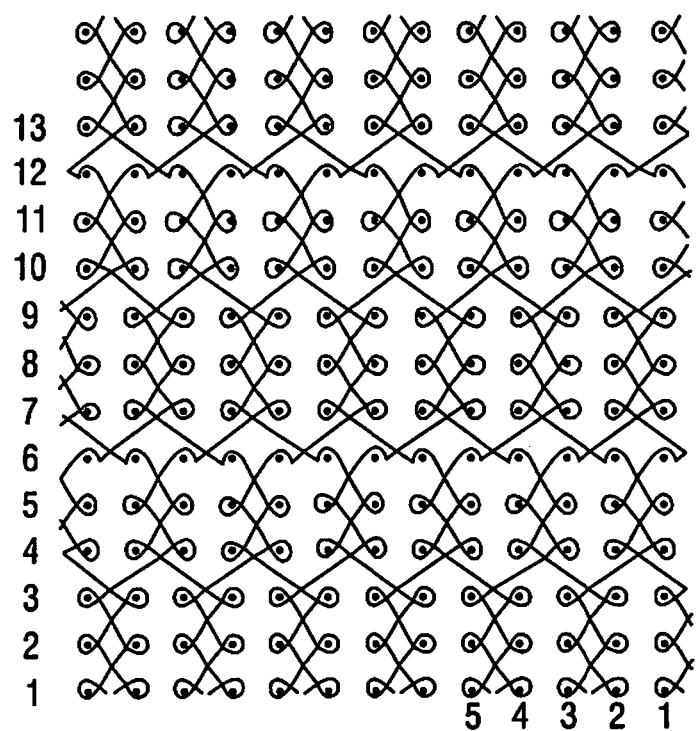

The isoelastic porous mesh is formed on a warp knitting machine or raschel knitting machine. As shown in the knitting graphic of FIG. 2A, the overall pattern repetition size of the knit isoelastic porous mesh may be twelve (12) courses. FIG. 2A depicts only one front thread and one back thread to better show the movement of the thread. The evolution of the threads at the thirteenth course is the same as at the first course. The isoelastic porous mesh is knitted using two guide-bars (❶ and ❷ in FIG. 2A). The first knitted course is represented at the bottom in FIG. 2B. The needles are not represented on the knitting graphic, but their position can be deduced from the columns of stitches. In embodiments, the threads move under a total of five needles. Due to the design of the warp knitting machine, the first needle is represented on the right in FIG. 2B.

Figure 3:
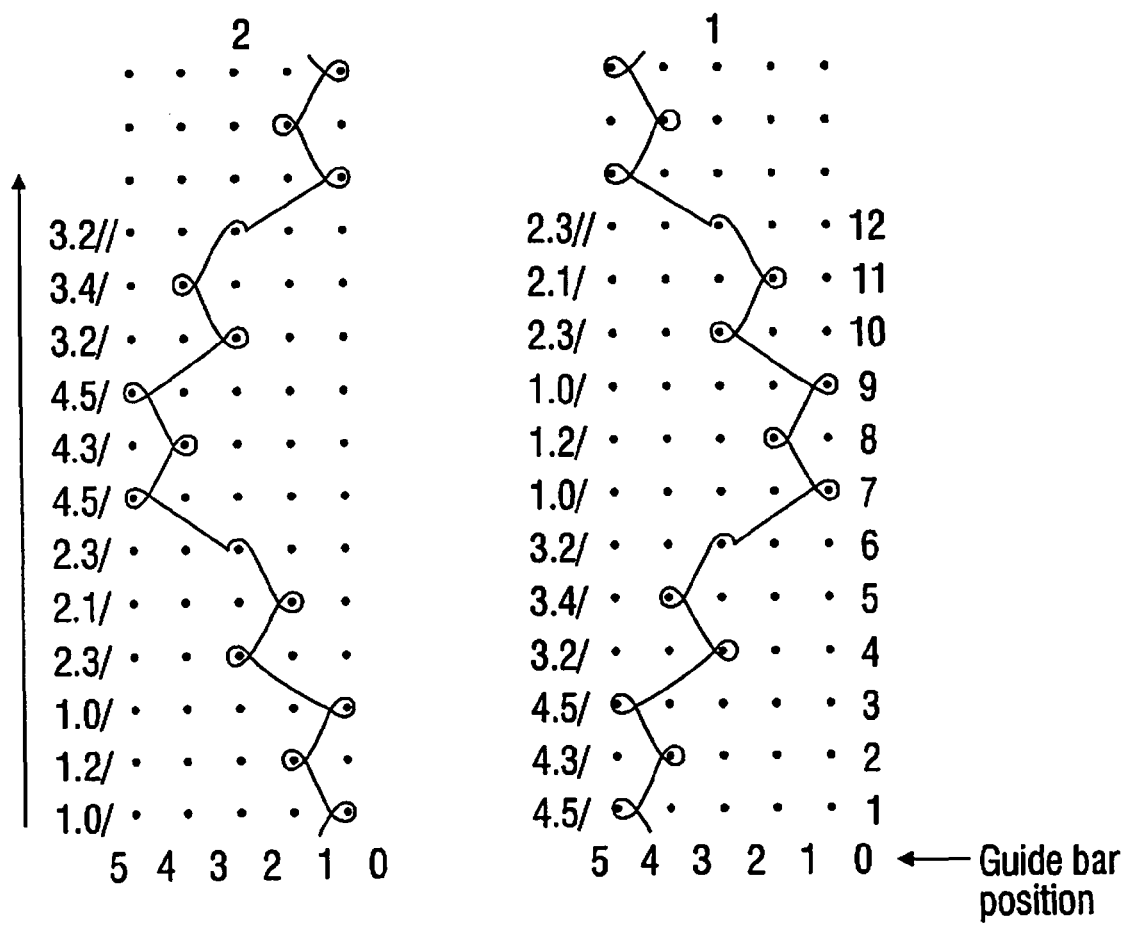
FIG. 3 is a schematic of the guide bar position during knitting of an isoelastic porous mesh in accordance with the present disclosure.

The graphic of FIG. 3 shows the movement of guide bars of a knitting machine used to form an isoelastic porous mesh in accordance with embodiments of the present disclosure. The guide-bars' movements are read from bottom to top, because the first knitted course is at the bottom. Since the first needle is represented at the extreme right of the graphic, the zero point is located at the right of the first needle.

The movements of the two guide-bars according to ISO 11676 pattern nomenclature are the following:
Front bar: 1-0/1-2/1-0/2-3/2-1/2-3/4-5/4-3/4-5/3-2/3-4/3-2//
Rear bar: 4-5/4-3/4-5/3-2/3-4/3-2/1-0/1-2/1-0/2-3/2-1/2-3//

A knit mesh based on the above knitting scheme produces a majority of pores greater than about 1.0 mm in diameter. In embodiments, 90% of the porosity of the mesh is provided by pores having a diameter greater than 1 mm. These pores maintain their diameter when exposed to small physiological loads. In embodiments, the principal pores 12 retain a diameter of at least 1.0 mm when the mesh is subjected to forces up to 25 N from any of the warp direction, the weft direction and the diagonal direction.

Figure 4:
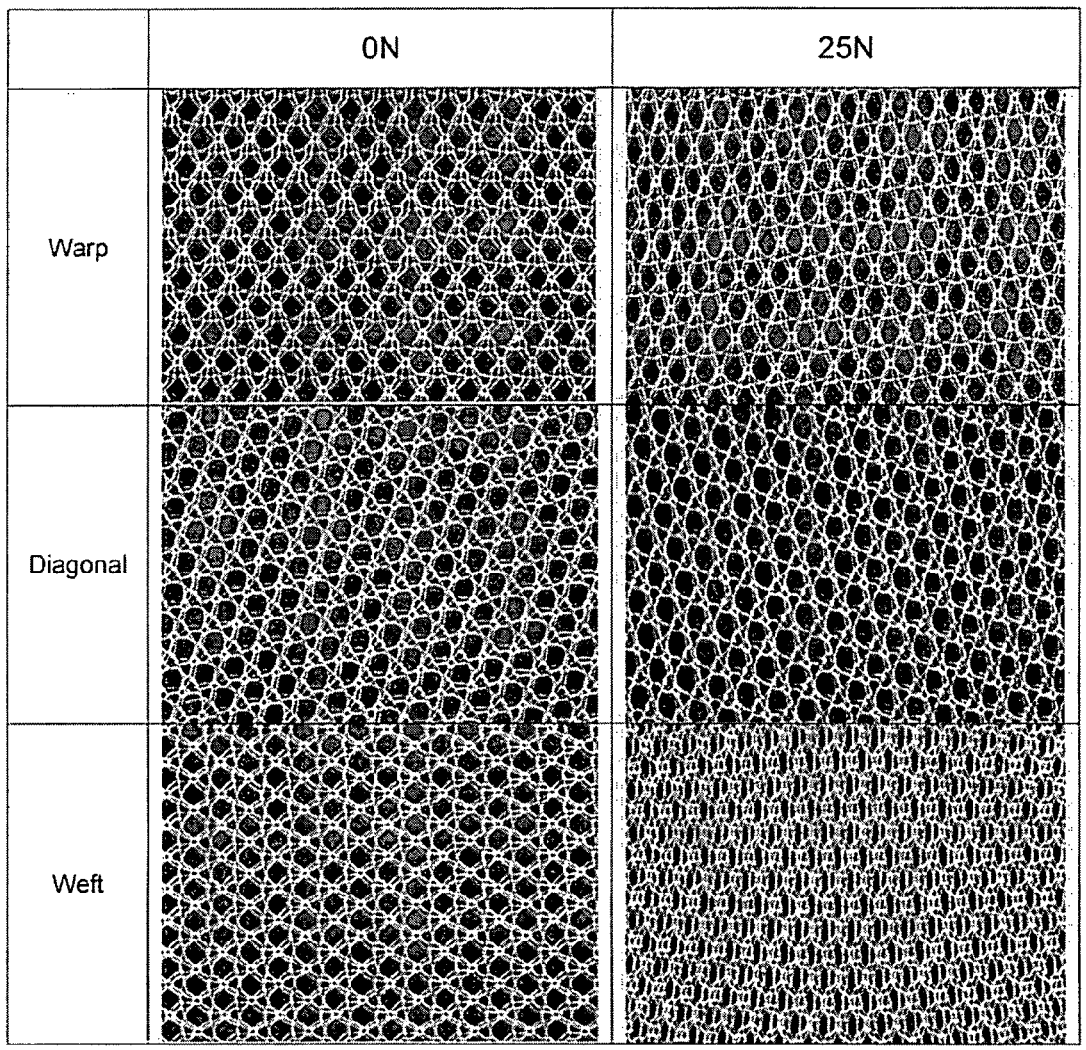
FIG. 4 is a front view of deformation of the pores of a mesh of the prior art under no load and a load of 25 Newtons.

During and/or following implantation, a mesh may elongate. This elongation can lead to occlusion of the pores of some prior art meshes, as shown in FIG. 4. The occlusion of the pores may inhibit or prevent tissue ingrowth, integration, and healing of the wound repaired by the mesh.

FIG. 4 is a front view of deformation of the pores of a mesh of the prior art under no load and a load of 25 N. The mesh shown in FIG. 4 was manufactured using 100 μm diameter polypropylene monofilament according to the knitting scheme of the prior art as is disclosed in U.S. Pat. No. 6,408, 656. As seen in FIG. 4, significant deformation of the pores of the mesh occurs under loads as small as 25 N, especially in the weft direction. As the load is increased, the deformation of the pores also increases to near occlusion in the weft and warp directions under a 75 N load.

Figure 5:
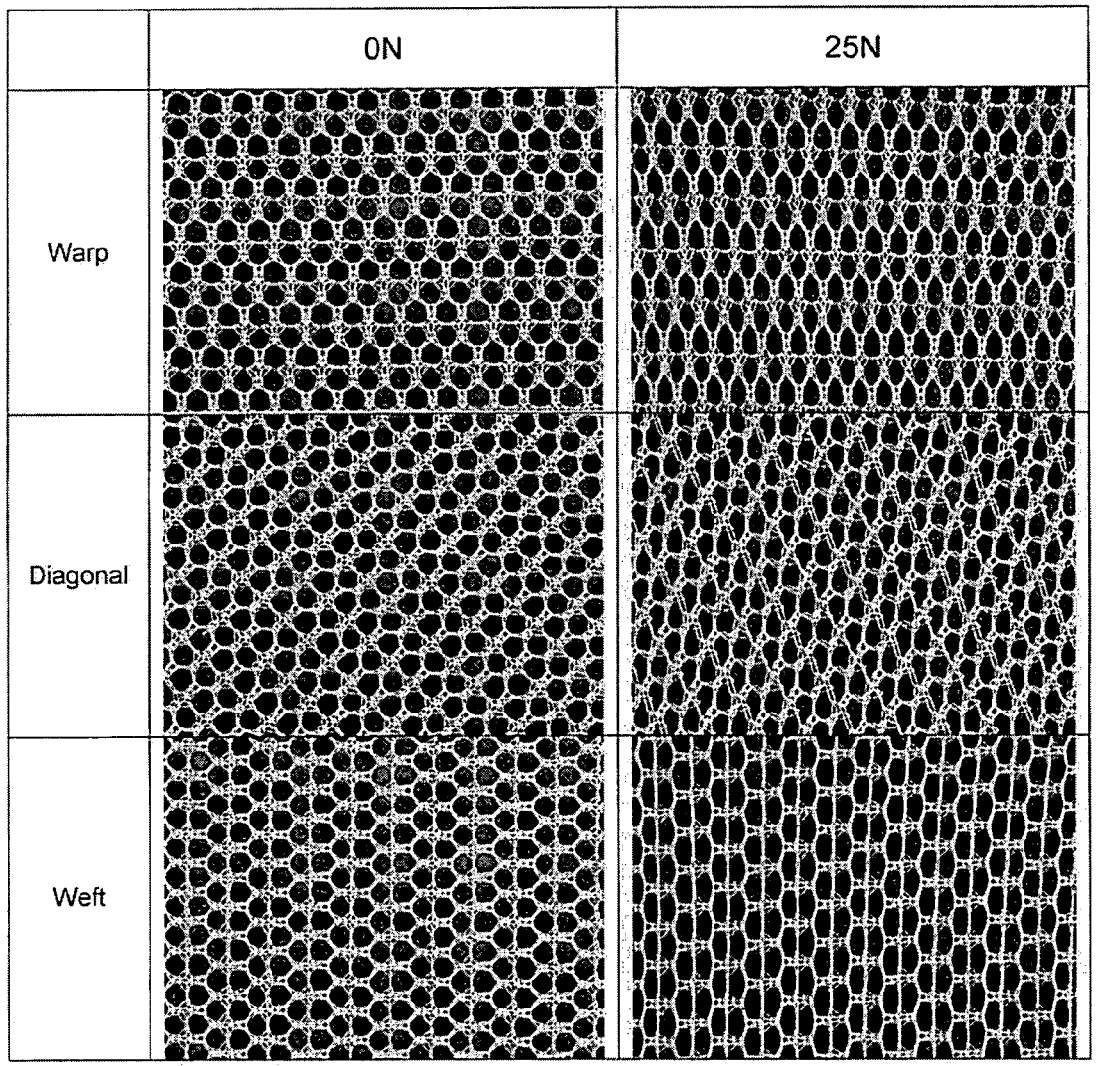
FIG. 5 is a front view of deformation of the pores of an isoelastic porous mesh of the present disclosure under no load and a load of 25 Newtons.

The pores of the isoelastic porous mesh of the present disclosure remain open under physiological loads, allowing for tissue ingrowth, integration of the mesh, and repair of the tissue. FIG. 5 is a front view of the deformation of the pores of isoelastic porous meshes in accordance with an embodiment of the present disclosure under no load and at 25 N. The isoelastic porous mesh shown in FIG. 5 was manufactured using the knitting scheme disclosed above using 0.08 mm monofilament of non-biodegradable polyethylene terephthalate (PET). As shown in FIG. 5, the diameter of the pores does not vary significantly when the isoelastic porous mesh of the disclosure is subjected to loads of 25 N from any of the warp direction, the weft direction or the diagonal direction. Additionally, while some further deformation of the pores may occur at loads greater than 25 N, this deformation does not cause occlusion of the pores even at loads as great as 75 N. Rather, a substantial percentage of the original porosity of the mesh remains even at such high loads.

Physical properties of the isoelastic porous mesh, when measured for the entire mesh, may vary depending on the nature of the filament employed in making the mesh (e.g., the specific polymer employed, the use of monofilaments or multifilaments to make the mesh, the diameter of the filaments used to make the mesh, etc.). In embodiments, the density of a mesh in accordance with the present disclosure is from about 35 g/m$^2$ to about 55 g/m$^2$, in embodiments about 45 g/m$^2$.

Certain mechanical properties, such as tensile breaking strength, tensile elongation under 50 N, and tear strength, may be measured in both a warp direction and a weft direction. In embodiments, a mesh in accordance with the present disclosure has a tensile breaking strength in the warp direction from about 100 N to about 300 N, in embodiments from about 150 N to about 200 N, in embodiments about 180 N. In embodiments, a mesh in accordance with the present disclosure has a tensile breaking strength in the weft direction from about 100 N to about 300 N, in embodiments from about 150 N to about 200 N, in embodiments about 140 N. In embodiments, a mesh in accordance with the present disclosure has a tensile elongation under 50 N of about 50% in the warp direction. In embodiments, a mesh in accordance with the present disclosure has a tensile elongation under 50 N of about 50% in the weft direction. In embodiments, a mesh in accordance with the present disclosure has a tear strength in the warp direction from about 20 N to about 30 N, in embodiments about 25 N. In embodiments, a mesh in accordance with the present disclosure has a tear strength in the weft direction from about 20 N to about 30 N, in embodiments about 25 N.

Tests used to determine the physical properties of the isoelastic porous mesh are known in the art, such as those provided by the International Organization for Standardization (ISO). For example, the following tests can be run on samples of the isoelastic porous mesh to determine the properties of the mesh:

Density:
ISO 3801: 1977 Determination of Mass per Unit Length and Mass per Unit Area Pore Size: Measured on a projector.

Tensile breaking strength and tensile elongation at 50 N:
ISO 13934-1: 1999 Determination of Breaking Strength and Elongation.

Tear Strength:
ISO 4674: 1977 standard—Method A1 Determination of Tear Resistance of Coated Fabrics. Surface density can be determined, for example, using a calibrated balance to weigh a given sample area. Tensile breaking strength, elongation under 50N, and tear strength can be tested on a machine such as the Hounsfield H5K5 Traction testing machine (Hounsfield, Redhill, England).

Any fiber-forming biocompatible polymer may be used to form the isoelastic porous mesh. The biocompatible polymer may be synthetic or natural. The biocompatible polymer may be biodegradable, non-biodegradable or a combination of biodegradable and non-biodegradable. The term "biodegradable" as used herein is defined to include both bioabsorbable and bioresorbable materials. By biodegradable, it is meant that the materials decompose, or lose structural integrity under body conditions (e.g., enzymatic degradation or hydrolysis) or are broken down (physically or chemically) under physiologic conditions in the body such that the degradation products are excretable or absorbable by the body.

The biocompatible polymer may be selected from the group consisting of biodegradable polymers, non-biodegradable polymers, and combinations thereof.

Representative natural biodegradable polymers include: polysaccharides, such as chitin, hyaluronic acid, cellulose, and chemical derivatives thereof (substitutions and/or additions of chemical groups, for example, alkyl, alkylene, hydroxylations, oxidations, and other modifications routinely made by those skilled in the art); and proteins, such as casein and silk, and copolymers and blends thereof, alone or in combination with synthetic polymers.

Synthetically modified natural polymers which may be employed include cellulose derivatives, such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt. These are collectively referred to herein as "celluloses."

Representative synthetic degradable polymers which may be used include polyhydroxy acids prepared from lactone monomers, such as glycolide, lactide, caprolactone, ε-caprolactone, valerolactone, and δ-valerolactone, as well as pluronics, carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly(hydroxyvaleric acid); poly(lactide-co-(ε-caprolactone)); poly(glycolide-co-(ε-caprolactone)); polycarbonates; poly(pseudo amino acids); poly(amino acids); poly(hydroxyalkanoate)s; polyalkylene oxalates; polyoxaesters; polyanhydrides; polyortho esters; and copolymers, block copolymers, homopolymers, blends, and combinations thereof.

Some non-limiting examples of suitable non-bioabsorbable materials from which the present mesh may be made include: polyolefins, such as polyethylene and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins, such as fluoroethylenes, fluoropropylenes, fluoroPEGSs, and polytetrafluoroethylene; polyamides, such as nylon and polycaprolactam; polyamines; polyimines; polyesters, such as polyethylene terephthalate and polybutylene terephthalate; aliphatic polyesters; polyethers; polyether-esters, such as polybutester; polytetramethylene ether glycol; 1,4-butanediol; polyurethanes; acrylic polymers and copolymers; modacrylics; vinyl halide polymers and copolymers, such as polyvinyl chloride; polyvinyl alcohols; polyvinyl ethers, such as polyvinyl methyl ether; polyvinylidene halides, such as polyvinylidene fluoride and polyvinylidene chloride; polyacrylonitrile; polyaryletherketones; polyvinyl ketones; polyvinyl aromatics, such as polystyrene; polyvinyl esters, such as polyvinyl acetate; copolymers of vinyl monomers with each other and olefins, such as etheylene-methyl methacrylate copolymers, acrylonitrile-styrene copolymers, ABS resins, and ethylene-vinyl acetate copolymers; alkyd resins; polycarbonates; polyoxymethylenes; polyphosphazine; polyimides; epoxy resins; aramids, rayon; rayon-triacetate; spandex; silicones; and combinations thereof.

In embodiments, the biocompatible polymer is polyester. In embodiments, the polyester is polyethylene terephthalate.

The thread used to form the isoelastic porous mesh may be monofilament or multifilament. In embodiments, the biocompatible polymer filament is a monofilament. In embodiments where the thread is monofilament, the monofilament can have a diameter from about 0.05 mm to about 0.15 mm, in embodiments about 0.08 mm. In embodiments, the thread is a multifilament thread.

Following knitting, the isoelastic porous mesh can be packaged and sterilized using conventionally known techniques. The isoelastic porous mesh can be used as provided in the package or cut to any desired dimension once removed from the package.

In use, the isoelastic porous mesh can be implanted either in an extraperitoneal site (between the abdominal wall and the peritoneum) or in a premuscular site (before the deep muscular plane) via an open or a laparoscopic approach. For example, the isoelastic porous mesh can be fixed to the Cooper's ligament and/or to the anterior muscular plane. The isoelastic porous mesh can also be implanted between the posterior muscular plane and the anterior aponeurotic muscular plane (external oblique muscle). The isoelastic porous mesh can be used in the sizes provided or can be cut to any desired size. Fixation to the surrounding tissues can be achieved by stapling, conventional sutures or other means.

The isoelastic porous mesh of the disclosure may be positioned via a posterior access route and pass easily through a trocar by being folded or rolled. Once in place, the isoelastic porous mesh may be unfolded and the position adjusted. Accordingly, the isoelastic porous mesh may be used in both open surgery and minimally invasive surgical procedures.

While the above description contains many specifics, these specifics should not be construed as limitations on the scope of the present disclosure, but merely as exemplifications of preferred embodiments thereof. Those skilled in the art will envision many other possible variations that are within the scope and spirit of the present disclosure.

We claim:

1. An isoelastic porous mesh comprising a biocompatible polymer filament knit on a knitting machine according to a front bar knitting scheme of 1-0/1-2/1-0/2-3/2-1/2-3/4-5/4-3/4-5/3-2/3-4/3-2// and a rear bar knitting scheme of 4-5/4-3/4-5/3-2/3-4/3-2/1-0/1-2/1-0/2-3/2-1/2-3//, wherein the mesh includes pores which remain greater than 1 mm in diameter under a load of about 25N.

2. The isoelastic porous mesh according to claim 1, wherein the biocompatible polymer is selected from the group consisting of biodegradable polymers, non-biodegradable polymers, and combinations thereof.

3. The isoelastic porous mesh according to claim 1, wherein the biocompatible polymer is a non-biodegradable polymer.

4. The isoelastic porous mesh according to claim 3, wherein the biocompatible polymer is a polyester.

5. The isoelastic porous mesh according to claim 4, wherein the polyester is polyethylene terephthalate.

6. The isoelastic porous mesh according to claim 1, wherein the biocompatible polymer filament is a monofilament.

7. The isoelastic porous mesh according to claim 6, wherein the monofilament has a diameter of from about 0.05 mm to about 0.15 mm.

8. The isoelastic porous mesh according to claim 1, wherein at least 90% of the pores have a diameter of from about 1.0 mm to about 2 mm under no load.

9. The isoelastic porous mesh according to claim 8, wherein the pores remain unoccluded at loads as great as 75N.

10. A method of forming an isoelastic porous mesh comprising: knitting a mesh according to a front bar knitting scheme of 1-0/1-2/1-0/2-3/2-1/2-3/4-5/4-3/4-5/3-2/3-4/3-2// and a rear bar knitting scheme of 4-5/4-3/4-5/3-2/3-4/3-2/1-0/1-2/1-0/2-3/2-1/2-3//, wherein the mesh includes pores which remain greater than 1mm in diameter under a load of about 25N.

* * * * *